US006846826B2

(12) United States Patent  
Chen

(10) Patent No.: US 6,846,826 B2
(45) Date of Patent: *Jan. 25, 2005

(54) PHENOXYPROPANOL CONNECTED WITH PHENYLPIPERAZINE AND PHENOXYALKYLAMINE TERMINAL IN ITS SIDE CHAIN

(75) Inventor: Ing-Jun Chen, 10F, No. 148-95, Guang-Hwa 1st Rd., Kaohsiung (TW)

(73) Assignees: Ing-Jun Chen (TW); Tong-Ho Lin, Taipei ( * ) Notice: Subject to any disclaimer, the term of this patent is extended or adjusted under 35 U.S.C. 154(b) by 0 days.

This patent is subject to a terminal disclaimer.

(21) Appl. No.: 10/105,265

(22) Filed: Mar. 26, 2002

(65) Prior Publication Data

US 2003/0055066 A1 Mar. 20, 2003

(30) Foreign Application Priority Data

Mar. 30, 2001 (TW) ........................................ 90107935 A

(51) Int. Cl.[7] .................. A61K 31/496; A61K 31/4422; C07D 401/12; C07D 211/90
(52) U.S. Cl. .................. 514/253.13; 514/356; 544/365; 546/321
(58) Field of Search ...................... 544/365; 514/253.13, 514/356; 546/321, 322

(56) References Cited

U.S. PATENT DOCUMENTS

2002/0156109 A1 * 10/2002 Chen

FOREIGN PATENT DOCUMENTS

JP 2000-86633 * 3/2000

OTHER PUBLICATIONS

Khadikar et al. Indian Journal of Chemistry, vol. 33B, pp. 451–454 (1994).*

Asano et al., "Pharmacological Profiles of YM–16151–1 and Its Optical Isomers: A Novel Calcium Entry Blocking and Selective Beta–1 Adrenoceptor Blocking Agent," Journal of Pharmacology and Experimental Therapeutics, vol. 254, No. 1, pp. 204–211.

Ciaraldi et al., "Hormone Action at the Membrane Level— VII: Adrenergic Receptors in Rat Heart and Adipocytes and Their Modulation by Thyroxine," Biochemica et Biophysica Acta, vol. 541, 1978, pp. 334–346.

(List continued on next page.)

Primary Examiner—Emily Bernhardt
(74) Attorney, Agent, or Firm—Birch, Stewart, Kolasch & Birch, LLP

(57) ABSTRACT

Certain 1,4-dihydropyridine compounds, useful as adrenergic blocking agents and as calcium channel blocking agents, the compounds having the formula

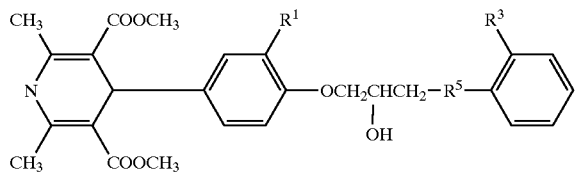

wherein $R^1$ is hydrogen, halogen, $C_{1-6}$-alkyl, or $C_{1-6}$-alkoxy, $R^3$ is hydrogen, halogen, $C_{1-6}$-alkyl, $C_{1-6}$-alkoxy, or $CF_3$ $(CH_2)_nO$— wherein n is 1, 2, or 3, and $R^5$ is —$NHCH_2CH_2O$— or —$N(CH_2CH_2)_2N$—.

11 Claims, 3 Drawing Sheets

YM 430

YM 1615-1

OTHER PUBLICATIONS

Chen et al., "Capsinolol: the first β–adrenoceptor blocker with an associated calcitonin gene–related peptide releasing activity in the heart," British Journal of Pharmacology, vol 119, 1996, pp. 7–14.

Chen et al., "Eugenolol: An Eugenol–Derived β–Adrenoceptor Blocker with Partial $\beta_2$–Agonist and Calcium Mobilization Inhibition Associated Vasorelaxant Activities," Drug Development Research, vol. 40, 1997, pp. 239–250.

Chen et al., "Xanthonolol: A Calcium Channel and Beta–Adrenoceptor Blocker with Vasodilating Properties," Gen. Pharmac., vol. 24, No. 6, 1993, pp. 1425–1433.

Huang et al., "Eugenodilol: A Third–Generation β–Adrenoceptor Blocker, Derived from Eugenol, with α–Adrenoceptor Blocking and $\beta_2$–Adrenoceptor Agonist–Associated Vasorelaxant Activities," Journal of Cardiovascular Pharmacology, vol. 34, 1999, pp. 10–20.

Huang et al., "Ferulidilol: A Vasodilatory and Antioxidant Adrenoceptor and Calcium Entry Blocker, with Ancillary $\beta_2$–Agonist Activity," Drug Development Research, vol. 47, 1999, pp. 77–89.

Liang et al., "Labedipinedilol–A: A Vanilloid–Based α/β–Adrenoceptor Blocker with Calcium Entry Blocking and Long–Acting Antihypertensive Properties," Drug Development Research, vol. 49, 2000, pp. 94–108.

Lin et al., "Vasomolol: An Ultra Short–Acting and Vasorelaxant Vanilloid Type $\beta_1$–Adrenoceptor Antagonist," Journal of Cardiovascular Pharmacology, vol. 28, 1996, pp. 149–157.

O'Donnell et al., "The Contribution of Extraneural Uptake to the Trachea–Blood Vessel Selectivity of β–Adrenoceptor Stimulants in vitro in Guinea–Pigs," Br. J. Pharmac., vol. 57, 1976, pp. 369–373.

O'Donnell et al., "The Importance of Choice of Agonist in Studies Designed to Predict $\beta_2$:$\beta_1$ Adrenoceptor Selectivity of Antagonists from $pA_2$ Values on Guinea–Pig Trachea and Atria," Naunyn–Schmiedeberg's Arch. Pharmacol., vol. 308, 1979, pp. 183–190.

Porzig et al., "Competitive and Non–Competitive Interactions Between Specific Ligands and Beta–Adrenoceptors in Living Cardiac Cells*," Nauyn–Schmiedeberg's Arch. Pharmacol., vol. 321, 1982, pp. 89–99.

Ruffolo Jr. et al., "Recent Observations with β–Adrenoceptor Blockade: Beneficial Effects in Hypertension and Heart Failure," American Journal of Hypertension, vol. 11, 1998, pp. 9S–14S.

Sheu et al., "Vanidilol: A vanilloid–Type Vasorelaxant and Ocular Hypertensive Beta–Adrenoceptor Blocker with Partial Beta–2–Agonist Activity," Pharmacology, vol. 54, 1997, pp. 211–224.

Yamamoto et al., "Pharmacologic Characterization of FR172516: A New Combined Calcium Channel–Blocking and β–Adrenoceptor–Blocking Agent," Journal of Cardiovascular Pharmacology, vol. 33, 1999, pp. 587–594.

Yeh et al., "Isoeugenodilol: A Vasorelaxant α/β–Adrenoceptor Blocker with Antioxidant Activity," Drug Development Research, vol. 51, 2000, pp. 29–42.

Yeh et al., "Third–Generation Dihydropyridine–Type Calcium Channel Blocker Labedipinedilol–B Displays α/β–Adrenoceptor Blocking Activities," Drug Development Research, vol. 52 2001, pp. 462–474.

Yeh et al., "Vanidipinedilol: A Vanilloid–Based β–Adrenooceptor Blocker Displaying Calcium Entry Blocking and Vasorelaxant Activities," Journal of Cardiovascular Pharmacology, vol. 35, 2000, pp. 51–63.

Wu et al., "A Highly Selective $\beta_1$–Adrenergic Blocker with Partial $\beta_2$Agonist Activity Derived from Ferulic Acid, an Active Component of *Ligusticum wallichii* Franch," Journal of Cardiovascular Pharmacology, vol. 31, 1998, pp. 750–757.

Wu et al., "Zingeronolol: A Newly Developed β–Adrenergic Blocking Agent Derived from Zingerone, A Pungent Principle of Ginger," Asia Pacific Journal of Pharmacology, vol. 11, 1996, pp. 5–12.

Shibasaki et al. Amtianginal Effects of YM430, a Novel Calcium Entry–Blocking and β–Adrenoceptor–Blocking Agent in Several Experimental Angina Models, Gen. Pharmac. vol. 29, No. 4, pp. 545–550, 1997.

Yamamoto et al., Pharmacologic Characterization of FR172516: A New Combined Calcium Channel–Blocking and β–Adrenoceptor–Blocking Agent, Journal of Cardiovascular Pharmacology pp. 587–594, vol. 33, No. 4, 1999.

Yeh et al., Vanidipinedilol: A Vanilloid–Based β–Andrenoceptor Blocker Displaying Calcium Entry Blocking and Vasorelaxant Activities, Journal of Cardiovascular Pharmacology, vol. 35, No. 1, 2000. pp. 51–63.

Buhler, Cardiovascular care with the new T–type clacium channel antagonist: possible role of attendant sympathetic nervous system inhibition, Journal of Hypertension 1997, vol. 15, p. 3–7.

Ruffolo Jr. et al., Carvedilol: A Novel Cardiovascular Drug with Multiple Actions, Cardiovascular Drug Reviews, vol. 10, No. 2, pp. 127–157, 1992.

* cited by examiner

PHENOXYPROPANOL CONNECTED WITH PHENYLPIPERAZINE AND PHENOXYALKYLAMINE TERMINAL IN ITS SIDE CHAIN

FIELD OF THE INVENTION

The present invention provides 1,4-dihydropyridine derivatives that may be used to continuously maintain hypotension. These compounds operate by blocking β-adrenoreceptor and calcium ion channel activity. They can also be used to block α-adrenoreceptor activity, thereby inducing a vasorelaxing effect. The 1,4-dihydropyridine derivatives of this invention have a guaiacoxy propanol amino ethoxy benzene or guaiacoxy propanol piperazinyl benzene side chain linked through a phenyl ring to the dihydropyridine nucleus. The side chain with α-adrenoreceptor blocking activity associated therewith, that is, an aminoethoxy benzene or a piperazinyl benzene, attached through a phenyl ring to a dihydropyridine nucleus, is a significant feature of this invention.

1. Background of the Invention

Ruffolo R R Jr, et al. have reported the antihypertensive agent, such as carvedilol, with multiple actions, including α-adrenocptor, β-adrenoceptor and relatively mild calcium channel blocking activities, has been introduced into the practice of medicine for the treatment of cardiovascular disease [*Drug Rev.* Vol.10, pp.127–157, 1992]. Calcium entry blockers lower blood pressure, relieve angina pectoris and improve chronic heart failure, primarily through peripheral and coronary vasodilation. However, Bühler F R. have reported among types of calcium antagonist, 1,4-dihydropyridine type may be involved in excess cardiac mortality has raised new controversies [*J. Hypertens* Vol.15, pp.S3–7, 1997]. In this field, Yeh J L et al. also said several 1,4-dihydropyridine derivatives, including our previous reported vanidipinedilol [*J. Cardiovasc Pharmacol.* Vol.35, pp.51–63, 1999], predominately with calcium channel antagonist activity and having additional β-adrenoceptor blocking activities, Nobuhiro Y et al. have been prepared to resolve this problem [Asano et al., 1990; Uchida et al. 1993; Shibasaki et al., 1997; Yeh et al., 1999; *J. Cardiovasc Pharmacol.* Vol.33, pp.587–594,1999]. In contrast, Ruffolo R R et al. the third generation β-adrenoceptor blocker such as labetalol, carvedilol, and our previous reported ferulidilol and eugenodilol, with β- and α-adrenoceptor blocking activities, have been suggested to treat hypertension and heart failure [*Am. J. Hypertens* Vol.11, pp.9S–14S, 1998].

2. Descriotion of the Prior Art

During the past decade, various vanilloid-derived vasodilatory β-adrenoceptor blockers have been synthesized and investigated in our laboratory [Chen et al. 1996; Lin et al. 1996; Wu et al. 1996; Sheu et al. 1997; Chen et al. 1997; Huang et al. 1999; Yeh et al. 1999]. That for the objective to overcome the tachycardia tendency due to the direct effect of peripheral vasodilator. In this research, the invention further created an unique vanilloid-based β-adrenoceptor blocker, which belongs to the 1,4-dihydropyridine derivative, chemically with guaiacoxypropanol-aminoethoxy benzene or guaiacoxypropanolpiperazinyl benzene moiety and pharmacologically with added α-adrenoceptor blocking activity, derived from aminoethoxy benzene or piperazinyl benzene moiety.

Furthermore, Asano, M. (*J. Pharmacol.* Vol.296, pp. 2004–211, 1990) has suggested YM-16151-1, and Shibasaki, K. (*Gen. Pharmac.* Vol.29, pp. 545–550,1997) has demonstrated YM 430. Though both these two compounds have β-adrenoceptor blocking effects as shown in FIG. 1, their structures are different from this invention.

SUMMARY OF THE INVENTION

Therefore, this invention provides structural embellishment, and associated synthetic methods, of 1,4-dihydropyridine derivatives chemically shown as Formula I, with guaiacoxypropanol-aminoethoxy benzene or guaiacoxypropanol piperaxinyl benzene moieties.

This invention will also make use of various pharmacological experiments to demonstrate that 1,4-dihydropiridine derivative could continuously maintain hypotension; with inhibition of β-adrenoreceptor and calcium ionchannel; induced vasorelaxing effect; and with a inhibition of α-adrenoreceptor.

This invention will further demonstrate that having 1,4-dihydropiridine derivatives chemically with guaiacoxypropanol-aminoethoxy benzene and guaiacoxy propanol piperazinyl benzene moiety as the main component, and adding necessary excipients to form various pharmacological compounds is therapeutically efficient.

DETAILED DESCRIPTION OF THE INVENTION

Figure 1:
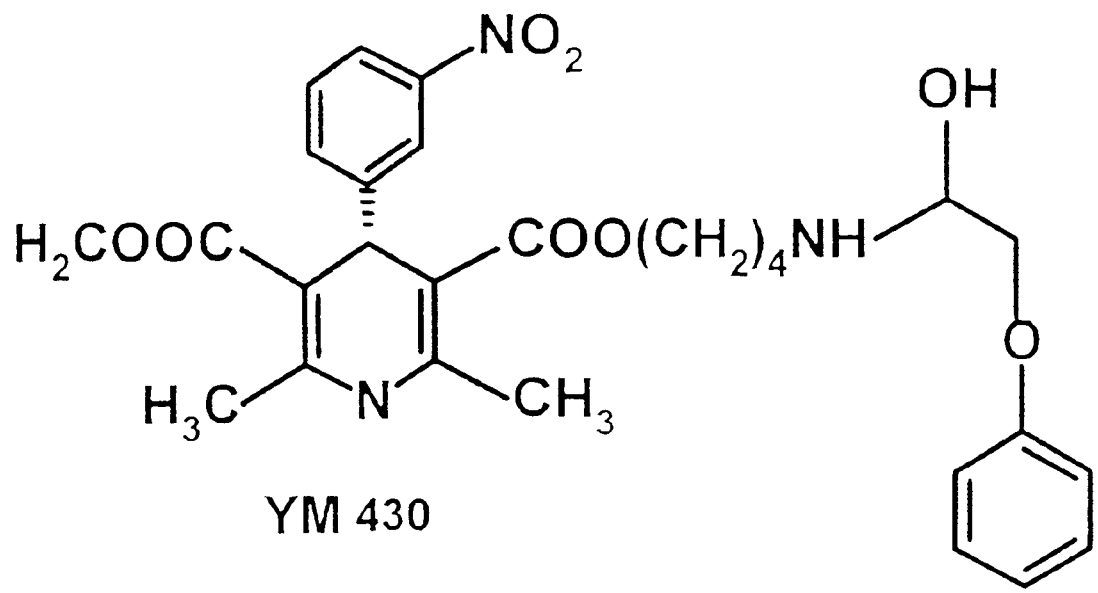
FIG. 1 depicts the structures of YM-16151-1 and YM 430.
Figure 1:
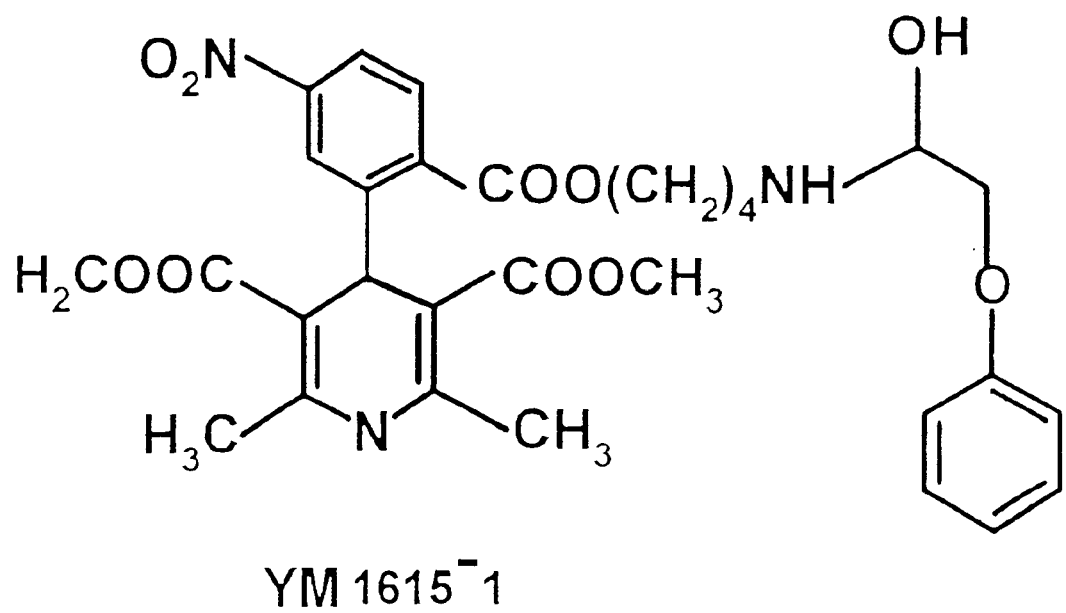
Figure 2:
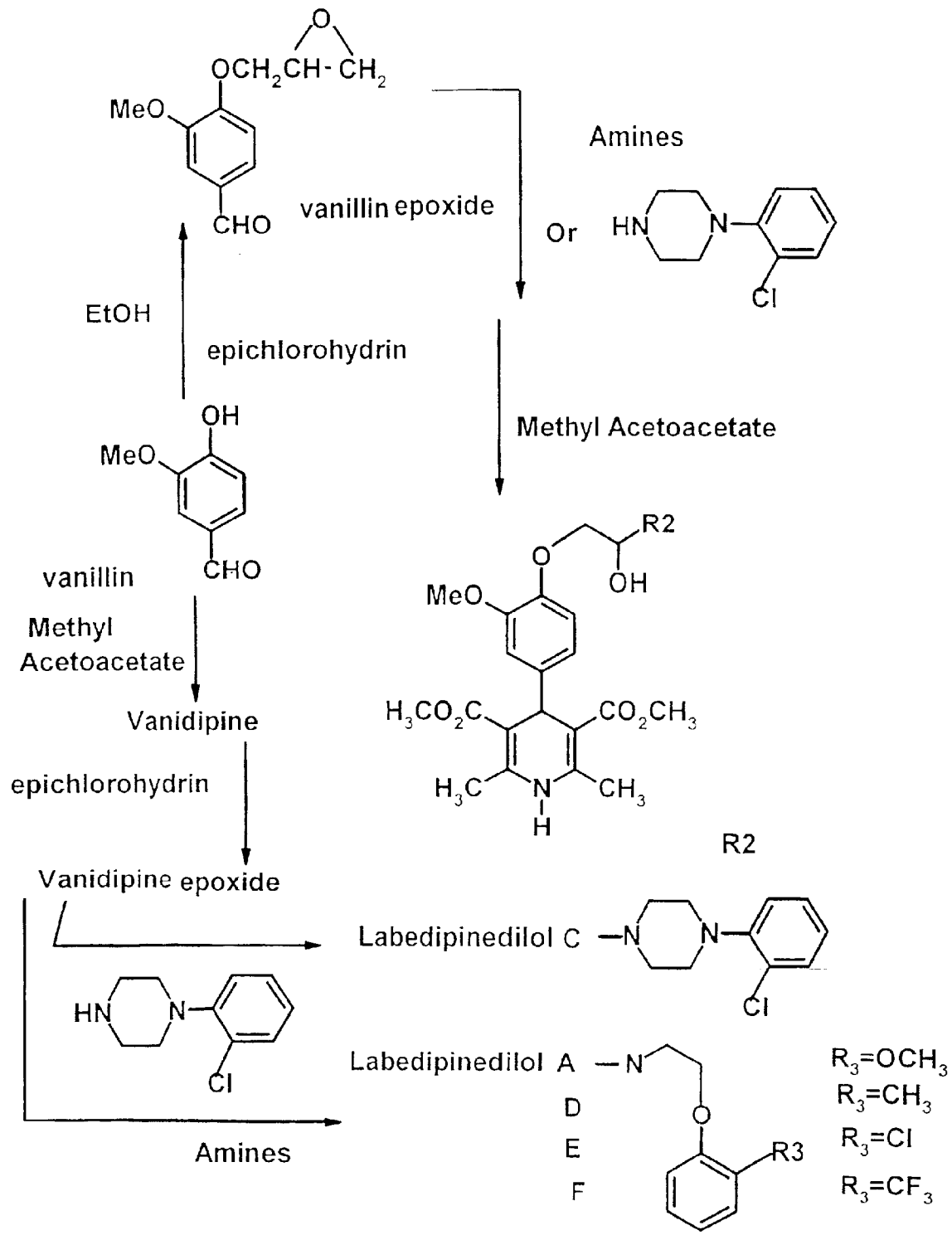
FIG. 2 depicts the method for synthesizing compounds of formula I.
Figure 3:
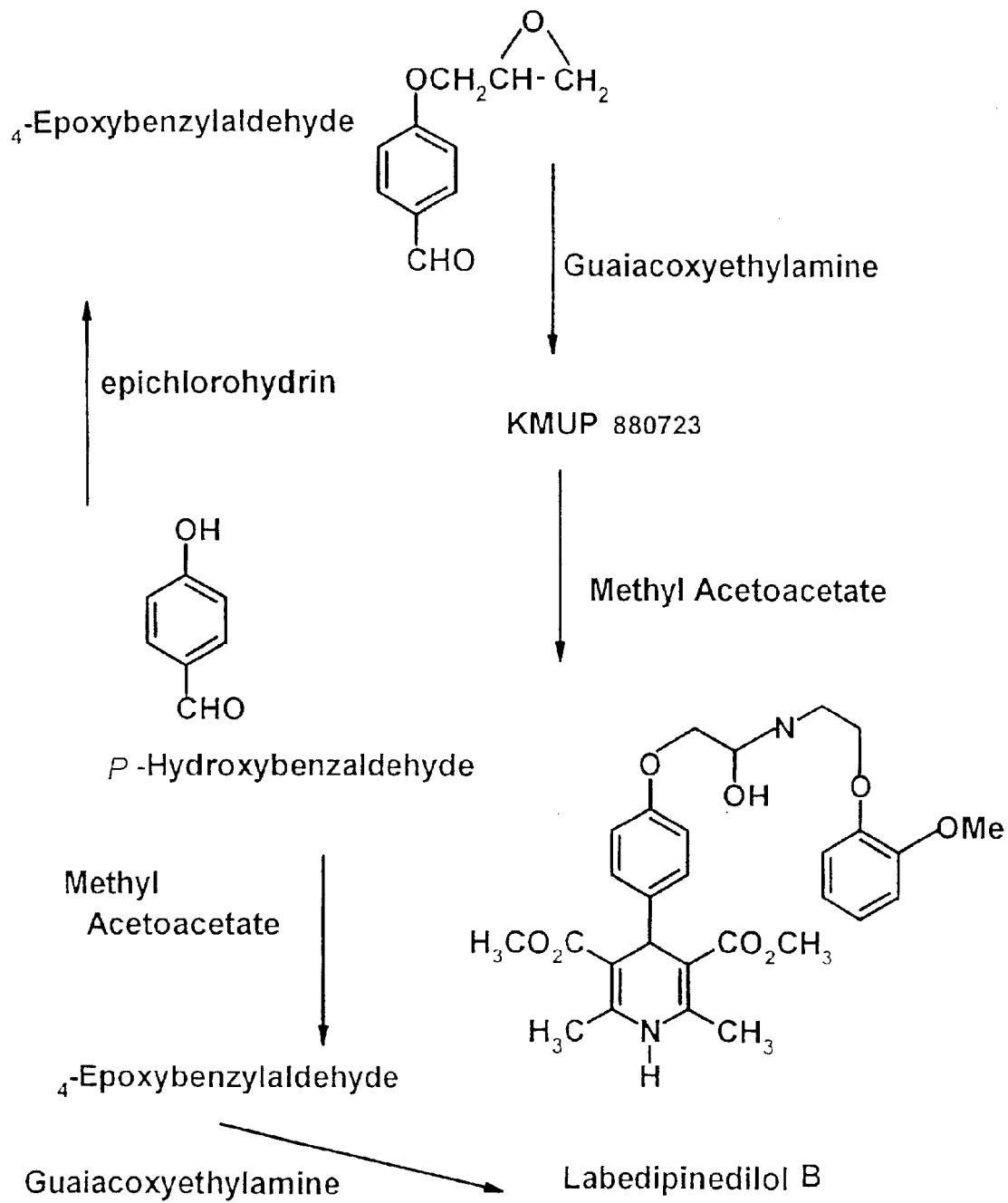
FIG. 3 depicts the method for synthesizing labedipinedilol B.

The invention discloses a 1,4-dihydropyridine derivative chemically modified with a gualacoxypropanolamine moiety. The compounds of this invention have the formula I,

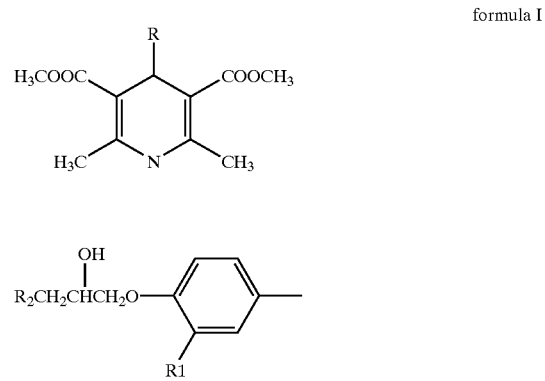

formula I wherein R represents
in which $R_1$ is selected from halogen (X), hydrogen (H), saturated $C_{1-C6}$ alkyl chain, saturated $C_{1-C6}$ alkoxy chain, and $R_2$ is selected from

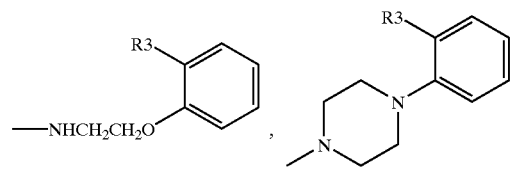

Aminoethoxy Benzene Terminal Piperazinyl Beuzene Terminal
and $R^3$ is selected from halogen (X), hydrogen (H), saturated $C_{1-C6}$ alkyl chain, saturated $C_{1-C6}$ alkoxy chain and $O-(C_1-C_3)-CF_3$. The derivatives of this invention can continuously maintain hypotension and induce a vasorelaxing effect, by inhibition of β-adrenoreceptors, α-adrenoreceptors, and calcium ion channels in the cardiovascular system.

The synthesis methods of Formula I, must have vanillin epoxide first. Placed vanillin and ethanol in a bottle, and reaction under alkaline condition; then epichlorohydrine is added for diffusion. Upon reaction and pressurized reduction. The vanillin epoxide is obtained through purification by silica gel chromatography. This invention of 1,4-dihydropiridine derivatives chemically shown as Formula I with guaiacoxypropanolamine moiety, that have structures embellished from basic nucleus of vanillin epoxide. The major purpose, draw into aromatic amine groups, or halogenic phenyl piperazine at the four location aldehyde group of vanillin epoxide. As reaction with vanillin epoxide and methyl acetoacetate, two hydroxyl aromatic group aldehyde at the Formula I come into being.

The said aromatic amine groups selected from guaiacoxyethylamine, 2-(2-trifluroethoxyphenoxy)ethylamine, 2-methylphenoxyethylamine, 2-(2-methylphenoxy)ethylamine, (2-(2-nitrophenoxy)ethylamine, 2-(2-halophenoxy)ethylamine and 2-(2-trifluorophenoxy)ethylamine. The halogenic phenyl piperazine have substitute halogenic phenyl groups at the first location of piperazine. The said halogen is fluorine, chlorine, bromine and iodine. The halogenic compound groups usually obtained as the halogenation reacted with halogen.

Specifically, the invention disclosed labedipinedilols compound synthesis methods, that are reacted vanidipine epoxide with aromatic amine groups. The said aromatic amine groups are selected from 2-(2-trifluoromethylphenoxy)ethylamine, guaiacoxyethylamine, 2-(2-trifluroethoxyphenoxy)ethylamine, (2-phenoxy)ethylamine, 2-Chlorophenoxyethylamine, and 2-methylphenoxyethylamine.

Synthesis compound of guaiacoxyethylamine that are heated guaiacol and 2-Bromoethylamine hydrobromide, stirred with NaOH till the pH value to 7. Upon cooling, the mixed solution's organic layer is extracted with chloroform and resing the extracted solids with NaCl and $MgSO_4$. re-crystallization until white crystallization is obtained.

In another synthesis of guaiacoxyethylainine, [guaiacoxy ethyl] phthalimide and hydrazine hydrate are dissolved in moisture-free alcohol for heating and diffusing. And stirred with HCl heat for continue diffusing. Upon cooling, after filtrating the extracted solids, NaOH is added to alkalize. The mixed solution's organic layer is extracted with chloroform and filtrating the extracted solids with potassium carbonate solution. The generated product is filled into silica gel columns utilizing the ratio of ethyl acetate as the diluent; upon purification, guaiacoxyethylamine are obtained.

Using halophenol and ethylene dibromide to perform 2-(2-halophenoxy)ethylamine as the above mentioned procedure of 2-(2-methylphenoxy) ethylamine synthesis methods. The said alkalize that drscribed the reaction procedure usually with alkali compounds, such as KOH, NaOH, $K_2CO_3$.

After purification and crystallization, the products a re individually tested for their physio-chemical information, including element analysis; MS, IR, $^1$H-NMR ($CDCl_3$), and UV etc. Appropriate experimental models are used to evaluate their pharmacological activities, thus ascertain the compound's activity.

Spontaneously hypertensive rat (SHR), an animal model exhibiting sustained hypertension, is usually used to evaluate the pre-clinical potential of any possible antihypertensive drugs. This study was designed to investigate the pharmacologic properties of labedipinedilols compounds, including its possible ability to bind to calcium channel and adrenoceptors, shown as Table 1 and 2.

The compound of this invention will include various excipients; carriers or diluents and pharmaceutically approved pH of processed salts in accordance to necessity to form composition with therapeutic efficacy. Such pharmaceutical preparation could be in solid form for oral and rectum administration; liquid form or non-intestinal injection form; or ointment form for direct application on affected part. Such solid forms are manufactured according to common pharmaceutical preparation methods, which will include disintegrant like starch; sodium carboxymethyl cellulose, adhesive like ethanol; glycerine, or magnesium stearic acid; lactose to make into pharmaceutical preparation like tablets or filled into capsules or suppository. Solution or saline that include this invention compound as ingredient could use buffers of phosphoric nature to adjust the pH to suitable level, before adding adjutant; emulsifier to produce injection dose or other liquid preparation. This invention compound or pharmaceutical manufacturing could mixed synthetic acid salts with various fundamental preparations to form ointments according to known pharmaceutical manufacturing methods. Pharmaceutical compounds manufactured with this invention compound being the major ingredient could be used on mammals to produce the efficacy of this main ingredient. General dosage could be adjusted according to the degree of symptoms, and normally a person will require 500 to 30000 mg each time, three times per day.

Pharmaceutical Activity

I. Confer the Heart Rate and Blood Pressure in Living Rat

HEART RATE AND BLOOD PRESSURE IN LIVING RAT

Male Wistar rats, weighing 200~300 g were abdominal anaesthetized with pentobarbital sodium. Tracheal was cannulated to maintain normal respiration. Polyethylene tube (inside diameter 0.58 mm, outside diameter 0.97 mm) was inserted into the left femoral vein to facilitate drug administration. A 3-way stopcock was used, with one end connected to a syringe for drug injection, while the other end was connected to the syringe filled with physiological saline. The latter was used to prevent residual drugs in the polyethylene tube after injection, which would affect experimental accuracy.

The right femoral artery was also inserted with polyethylene, and a 3-way stopcock was used tool, where one end was connected to heparin solution to prevent embolism. The other end was connected to a Disposable Diaphragm Dome, TA10019, and linked to a transducer. Through an amplifier, a recorder recorded the overall and average arterial pressure; heart rate to evaluate the effect of drug on blood pressure and heart rate. Different concentrations 0.5; 1.0; 3.0 mg/kg of compounds were given to the rats via femoral vein and the differences in the heart rate and blood pressure were compared. Furthermore in another group, test compounds of concentration 0.5; 1.0; 3.0 mg/kg were separately given to different rats via femoral vein, and the differences in the heart rate and blood pressure were compared.

II. Atrium on Isolated Rat Tissue and Tracheal on Isolated Guinea Pig Experiments The methods published by Chen, I. J et al. (*Gen Pharmacol.* Vol. 24, pp. 1425–1433, 1993) and by Yeh et al. (*J. Cardiovasc. Pharm.* Vol. 35, pp. 51–63, 2000) were referenced and modified.

The entire heart of rat (weighing 200~300 g) was removed immediately after the rat was sacrificed and the blood drained by incised carotid arteries, and placed in Kreb's solution equilibrated to a mixture of 95% $O_2$ and 5% $CO_2$ at room temperature (20~25° C.). The right and left atria were then separated.

The spontaneously-beating right atria was clipped on both end by heart shaped clips, where one end was fixed at the bottom of 10 ml of tissue bath made of physiological saline solution, and temperature maintained at 37° C. The other end of the atria was connected to a force transducer, and isometric contractions and beating rate of the right atria were recorded by COULBOURN AT-High-Speed VideoFigure. After the samples were given 250 mg of contractions and reach equilibrium the following experiments were carried out:

II-(1) Experiments on the Isolated Right Atrial Tissue of Rat

II-(1-a)α-Adrenoceptor Blocking Action

When the spontaneously beating rate of right atria reached a certain stability, cumulative administration of L-isoproterenol from $1\times10^{-10} \sim 3\times10^{-10}$ M caused the heart rate to increase continuously, and a cumulative dose-response curve was obtained. Then the L-isoproterenol was thoroughly washed off with Kreb's solution to recover the right atria's heart rate stability. After the equilibrum was reached again for at least 60 minutes, different concentrations ($10^{-7}$, $10^{-6}$, $10^{-5}$ M) of compounds were added. 30 minutes later, cumulative administration of L-isoproterenol from $1\times10^{-10}$ 18 $3\times10^{-10}$ M were carried out again, and another new cumulative dose-response curve was obtained. Administration of L-isoproterenol started from concentration $1\times10^{-10}$ M, and the concentration was raised 0.5 log each time for a total of six times. Cumulative administration interval was when the previous concentration reached its greatest effect, the next concentration would be immediately given. The time interval was approximately 3~5 minutes, and the $EC_{50}$ value could be obtained. From Schild plots, the $pA_2$ of compounds could be found. In other groups of rats, after separate administration of test compounds, their $pA_2$ values were obtained.

II-(1-b) Calculation of $pA_2$ Value

According to the method mentioned by Arunlakshana, O. et al.(Br. J. Pharmacol. Vol.14, pp. 48–57, 1959), which used the logarithm values of compound concentration testings as the x-coordinates, and the logarithm values of blocking agent of similar effect and (dose ratio)$^{-1}$ as the y-coordinates, the data obtained were plotted into Figures and the slope of regression found. From x-coordinates of the line of regression, the intercept value was found, which is the $pA_2$ value of the compound under testing. The equation is as follows:

$$pA_2 = -\text{Log}KB \quad \text{Log}(DRADJ - 1) = n\text{log}[B] - \text{Log}KB$$

$$DRADJ(\text{dose ratio adjusted}) = \frac{DR(\text{dose ratio})}{CF(\text{correction factor})}$$

[B]=Test compound concentration in moles
KB: equilibrium dissociation constant
n: value of slope
DR: test $EC_{50}$ divided by control $EC_{50}$
CF: $EC_{50}$ of second or third control groups divided by $EC_{50}$ of first control group II-(1-c) Effect of Compound on the Increase of Spontaneous Beating in Right Artrium Caused by $CaCl_2$ The right atrium of the rats was allowed to equilibrate in Kreb's solution for at least 60 minutes. When the spontaneous beating rate had reached a certain stability, $CaCl_2$ of different concentrations (3.0, 6.0, and 9.0 mM) were cumulatively administered, and the changes in the spontaneous beating of right artrium were observed. Then the right atrium was thoroughly washed with Kreb's solution for several times and re-equlibrated for at least 60 minutes before different concentrations ($10^{-7}$, $10^{-6}$, and $10^{-5}$ M) of compounds were administed. 30 minutes later, different concentrations (3.0, 6.0, and 9.0 mM) were cumulatively administed, and the changes in the spontaneous beating of right artrium were observed again. The effect of $CaCl_2$ on the changes of spontaneous beating in right artrium were compared with and without the presence of compounds.

II-(2) Experiments on the Isolated Left Atrial Tissue of Rat

The inspontaneously-beating left atrial tissue was obtained from rat's isolated right atrial tissue experiments. Under similar conditions, contractions were induced in the right atria by approximately 1 volt of square waves which had a wave width about 2 msec wider than the threshold voltage. The contraction rate was 2 Hz and the resting tension 0.5 gm. After 60 minutes of equilibration, the following experiments were performed:

(a) Completion of cumulative concentration-response curve: similar to experimental method on isolated right atrium;

(b) Calculation of $pA_2$ value: similar to calculation method on isolated right atrium.

II-(3) Experiments on Guinea Pig's Isolated Tracheal

Guinea pigs of weight between 250~350 gm were used. 18~24 hours before the experiment, 5.0 mg/kg of reserpine was injected via abdominal cavity to prevent the discharge of catecholamines, when treated with phenoxybenzamine, that as suggested by O'Donnell and Wanstall (1979) experimental process.

After the guinea pigs were sacrificed, a slit was made along the neck, and a portion of tracheal approximately 4 cm long was removed. The tracheal was then placed in Kreb's solution aerated with a mixture of 95% $O_2$ and 5% $CO_2$ and maintained at room temperature about 22~25° C. After the surrounding tissue was carefully removed, the tracheal was cut into spiral shape with every turn having 3~4 cartilage segments, and divided according to the method suggested by Constantine (1965). The two ends of the tracheal were clamped with frog-heart shaped clamps, one end was fixed at the bottom of tissue bath filled with 200 ml of Kreb's solution, maintained at 37° C., while the other end was connected to a force transducer. Through a COULBOURN AT-High-Speed Videograph, long isometric contractions were recorded. After the sample was given 1.5 gm of tension and equilibrated, the following experiments were performed:

II-(3-a) Cumulative Concentration Response Curve

In the experiment, tracheal was first treated with 50 μm phenoxybenzamine for 30 minutes to prevent extraneuronal uptake, and reduce L-isoproterenol effect suggested by O'Donnell and Wanstall (1976). Then the tracheal was repeatedly washed with Kreb's solution for 20 minutes and $100^{-6}$ M of carbochol was added to cause contraction in the guinea pig's tracheal. When the contraction reached the maximum, every division of tracheal was used to complete two concentration response curve of L-isoproternol, one of them without administration of test compound and used as control; while the other curve was administered with $10^{-7}$, $10^{-6}$ and $10^{-5}$ M test compounds for 30 minutes before concentration response curve was completed. This is the test group.

II-(3-b) Calculation of $pA_2$

Similar to the calculation method for isolated right atrium experiment.

III. Discussion on the Direct Effect of Wistar Rat's Isolated Atria

With reference to the method suggested by Kaumann, A. J. et. al.(Naunyn-Schmiedeberg's Arch. Pharmacol. Vol. 311, pp. 205–218 and pp 237–248,1980). Wistar rats of weight between 20000~30000 gm were used. 18~24 hours before the experiment, 5 mg/kg of reserpine was injected via abdominal cavity to remove all endogenous catecholamines. Prior experiment, Wistar rats were sacrificed, the heart was immediately removed and placed in Kreb's solution aerated with air mixture and maintained at room temperature. The right and left atria were carefully separated. Then in accordance to the above mentioned experimental method, the effects of cumulative administration $10^{-10}$~$3\times10^{-4}$ M of test compounds.

IV Experiments on the Wistar Rat's Isolated Thoracic Aorta

After sacrificing Wistar rat of weight between 200~300 gm, the thoracic aorta was immediately removed and placed in cold Kreb's solution. The fatty connecting tissue surrounding the vessel wall was removed and the thoracic aorta was cut into rings of length 5 mm. The two ends of each ring was pieced and fixed with "Z" shaped platinum wires. Then the thoracic aorta was suspended in 10 ml of tissue bath, aerated with air mixture (95% $O_2$+5% $CO_2$) and maintained at 37° C., where one end was fixed at the bottom of tissue trough, the other end connected to force transducer to record the long contraction via recorder. The sample was given 1 gm of tension and equilibrated for 60 minutes before the following experiments were carried out.

IV-(1) Evalute α-Adrenoceptor Blocking Activity

After thoracic aorta had reached equilibrium in the tissue trough, cumulative administration of norepinephrine from $10^{-10}$~$3\times10^{-4}$ M caused the blood vessel contract to increase tension continuously, and a cumulative dose-response curve was obtained. Then the norepinephrine was thoroughly washed off with Kreb's solution to recover the aorta stability. After the equilibrium was reached again for at least 60 minutes, different concentrations as $10^{-7}$, $10^{-6}$, $10^{-5}$ M of test compounds were added. 30 minutes later, cumulative administration of norepinephrine from $1\times10^{-10}$~$3\times10^{-10}$ M were carried out again, and another new cumulative dose-response curve was obtained. Administration of norepinephrine started from concentration $1\times10^{-10}$ M, and the concentration was raised 0.5 log each time. Cumulative administration interval was when the previous concentration reached its greatest effect, the next concentration would be immediately given. The time interval was approximately 3~5 minutes, and the $EC_{50}$ value could be obtained. From Schild plots, the $pA_2$ of test compounds could be found. Calculation of $pA_2$ value: similar to calculation method on isolated right atrium.

IV-(2) Evalute Thoracic Aorta Contract Effect Induce by $CaCl_2$

After thoracic aorta had reached equilibrium in the tissue trough, cumulative administration of $CaCl_2$ from $10^{-10}$~$3\times10^{-4}$ M caused the blood vessel contract to increase tension continuously, and a cumulative dose-response curve was obtained. Then the $CaCl_2$ was thoroughly washed off with Kreb's solution to recover the aorta stability. After the equilibrum was reached again for at east 60 minutes, different concentrations as $10^{-8}$, $10^{-7}$, $10^{-6}$ M of test compounds were added. 30 minutes later, cumulative administration of $CaCl_2$ from $3\times10^{-5}$~$10^{-2}$ M were carried out again, and another new cumulative dose-response curve was obtained. Cumulative administration interval was when the previous concentration reached its greatest effect, the next concentration would be immediately given. The time interval was approximately 3~5 minutes, and the $EC_{50}$ value could be obtained. From Schild plots, the $pA_2$ of test compounds could be found. Calculation of $pA_2$ value: similar to calculation method on isolated right atrium.

V. Discussion on Characteristics of β-Receptor Binding

V-(1)Preparation of Cell Membrane at 4° C.

The membrane preparation for β-adrenoceptor binding assay was prepared according to the method of our previous study [Ciaraldi et al. (1978), and Petrus et al.(1988)]. The heart and lung of rat were removed and placed in cold Tris buffer.(250 mM sucrose, 1 mM $MgCl_2$, 50 mM Tris, pH 7.4). Then the atria and lung were separated and weighed, before placing in cold Tris buffer with volume 20× their weights. Using POLYTRON homogenizer at 15 seconds each time to crushed the tissue for 3~4 times before homogenization. The homogenized liquid was press filtered through gauze, and the filtered liquid was centrifuged at 70000 gm for 12 minutes. The centrifugal fluid was again centrifuged at 10,000 gm for 12 minutes. The second centrifugal fluid was centrifuged for the third time at 29,000 gm for 15 minutes. The pellet finally obtained was re-suspended in Tris buffer as little as possible. Then the method of Brodford et al.(1976) was adopted, where BSA (bovine serum albumin) was used as a standard, and protein assay dye was used to determine the protein content in the membrane. Finally, the protein concentration was diluted with Tris buffer to maintain 200~250 μg protein per 100 μl.

V-(2) Binding Assay on Receptor

The methods of Porzig et. al. (1982); Petrus (1988); and Muzzin et. al. (1974) were adopted with modifications. 100 μl of membranes; 50 μl of [³H]CGP-12177; 50 μl of test compound in various concentrations; eg. propranolol, labetalol, test compounds were mixed to obtain a final volume of 250 μl. This mixture was placed under 25° C. vibration and reacted for 60 minutes. After reaction, 1 ml of cold Tris buffer was added to terminate the binding reaction. Then Millipore filtration manifold and Whatman GF/C glass fiber were used for rapid press filtration, and 5 ml of cold Tris buffer was used to rinse the filtrate three times. After the filter paper with the filtrate was dried in a 60° C. oven for 3 hours, 4 ml of scintillation fluid was added, and Beckman LS6500 rackbeta liquid scintillation counter was used to determine the strength of radioactivity.

VI. Discussion on Characteristics of α-receptor Binding

VI-(1)Preparation of Cell Membrane at 4° C.

The membrane preparation for α-adrenoceptor binding assay was prepared according to the method of our previous study [Greengrass et al. (1979)]. The whole Wistar rats brain were placing in suspension buffer solution (0.25 mM sucrose, 5 mM Tris-HCl, pH 7.5). Then the brain were weight, before placing in cold Tris buffer with volume 20× their weights. Using POLYTRON homogenizer at 10 seconds each time to crushed the tissue for 3~4 times before homogenization. The homogenized liquid was press filtered through gauze, and the filtered liquid was centrifuged at 40,000 gm for 30 minutes. The pellet finally obtained was re-suspended in Tris buffer as little as possible. The result pellet was resuspended in the resuspension buffer solution ($MgCl_2$ 12.5 mM, Tris-HCl 62.5 mM, pH 7.5). Then the method of Brodford et al.(1976) was adopted, where BSA (bovine serum albumin) was used as a standard, and protein assay dye was used to determine the protein content in the membrane. Finally, the protein concentration was diluted with resuspension buffer solution to maintain 250~300 μg protein per 100 μl.

VI-(2) Binding Assay on Receptor

The methods of Letkowitz et. al. (1974) was adopted with modifications. 200 μl of membranes; 100 μl of [³H]prazosin; 100 μl of test compound in various concentrations; eg. labetalol, KMUP 880723, KMUP 880818, 100 μl of Tris buffer.(10 mM $MgCl_2$, 50 mM Tris, pH 7.5) were mixed to obtain a final volume of 500 μl. This mixture was placed under 25° C. vibration and reacted for 60 minutes. After reaction, 1 ml of cold Tris buffer was added to terminate the binding reaction. Then Millipore filtration manifold and Whatmnan GF/C glass fiber were used for rapid press filtration, and 5 ml of cold Tris buffer was used to rinse the filtrate three times. After the filter paper with the filtrate was dried in a 60° C. oven for 3 hours, 4 ml of scintillation fluid was added, and Beckman LS6500 rackbeta liquid scintillation counter was used to determine the strength of radioactivity.

VII. Discussion on Characteristics of Calcium Ion Binding

VII-(1) Preparation of Cell Membrane at 4° C.

The method of Tamazawa et. al. (1986) was modified and referenced. The cerebral cortex of rat was removed and placed in cold 0.85% NaCl solution. Then the cortex was weighed, before placing in cold 50 mM Tris-HCl solution and 100 mg ethylene diamino tetraacetic acid (EDTA) pH 7.7) with volume 9 times its weight. Using motor-driven Teflon homogenizer at 15 seconds each time to crushed the tissue for 3~4 times before homogenization. The homogenized liquid was press filtered through gauze, and the filtered liquid was centrifged at 900 gm for 10 minutes. The centrifugal fluid was centrifuged in order at 18,000 gm for 20 minutes, and 29,000 gm for 15 minutes again. The pellet finally obtained was rinsed with 50 mM Tris-HCD solution and 10 mg EDTA (pH 7.7) twice before resuspended in similar Tris-HCl solution and store at −80° C. Then the method of Brodford (1976) was adopted, where Bovine Serum Albumin (BSA) was used as a standard, and protein assay dye was used to determine the protein content in the membrane. Finally, the protein concentration was diluted with Tris-HCl solution to maintain at 4 mg/ml.

VII -(2) Binding Assay on Receptor

The methods of Gould et. al. (1982) was adopted with modifications. 100 µl of [$^3$H]nitrendipine, 100 µof Tris-HCl buffer solution, 200 µl of membranes, 100 µl of test compounds in various concentrationsn were mixed to obtain a final volume of 500 µl. This mixture was placed under 25° C. vibration and reacted in the dark for 60 minutes. Then Millipore filtration manifold and Whatman CF/C glass fiber were used for rapid press filtration, and 4 ml of cold Tris-HCl solution and 0.1 mM EDTA (pH 7.7) were used to rinse the filtrate four times. After the filter paper with the filtrate was dried in a 70° C. oven for 1 hours, 4 ml of scintillation fluid was added, and Beckman LS6500 rackbeta liquid scintillation counter was used to determine the strength of radioactivity.

VIII. Statistics Analysis

VIII.-(1) All values were presented in terms of mean±s.e.m. Student's t-test was applied to paired or unpaired observations and probability value (P) of less than 0.05 was considered to be significant.

VIII-(2) Calculation $ED_{50}$ and 95% depend on parts, according to the method used by Litchfield and Wilcoxon in 1949. Calculation for $pA_2$ value, according to the method used by Arunlakshana and Schild in 1959.

EXAMPLE 1

Synthesis Compound of Vanillin Epoxide 15 grams of vanillin and 900 ml of ethanol are placed in a bottle, and an equal molar of sodium hydroxide is added for reaction at 70° C. for 1 hour; 5 times molar of epichlorohydrine is added for diffusion at room temperature for two hours. Upon reaction and pressurized reduction, it is heated until it dissolves and upon filtration. The generated product is filled into silica gel columns utilizing the ratio of ethyl acetate:-hexane=1:1 as the diluent; upon purification, vanillin epoxide are obtained.

EXAMPLE 2

Synthesis Compound of Guaiacoxyethylamine 0.2 mole (22.4 ml) of guaiacol and 2-Bromoethylamine hydrobromide are heated to 100° C. while stirring vigorously, and within 30 minutes 125 ml of 1.6 N sodium hydroxide solution is added to continue the stirring and the pH value is adjusted to 7. Upon cooling, the mixed solution's organic layer is extracted with chloroform and rinsed with saturated 2 N sodium chloride solution and magnesium sulfate. The re-crystallization obtained is mixed with HCl and MeOH, white crystallized product, guaiacoxy ethylamine HCl is obtained.

EXAMPLE 3

Synthesis Compound of [Guaiacoxy Ethyl] Phthalimide

Using 0.2 mole (22.4 ml) of guaiacol and 34.6 ml (0.4 mole) ethylene dibromide to perform guaiacoxy ethylbromide as the above mentioned procedure of Example 2

36 grams (0.156 ml) of guaiacoxy ethylbromide and 27.3 grams (0.186 mole) of phthalimide are dissolved in 100 ml of dimethylacetamide, and stirred with heat for diffusion to 90° C. After 30 minutes, 10.45 g (0.186 mole) of potassium hydroxide is dissolved in 30 ml of methanol solution for heating and diffusing over 1.5 hours. Upon cooling, the mixed solution is poured into 300 ml of water. After filtrating the extracted solids, 200 ml of 10% potassium carbonate solution is added, and stirred with heat. The paste-like substance obtained is filtrated. After rinsing with tap water several times, moisture-free alcohol is used for re-crystallization until white crystallization is obtained.

EXAMPLE 4

Another Synthesis Method of Guaiacoxyethylamine 21 grams (0.071 ml) of [guaiacoxy ethyl] phthalimide and 3.55 grams (0.071 mol) of hydrazine hydrate are dissolved in 70 ml of moisture-free alcohol for heating and diffusing over 45 minute. And stirred with 20 ml 18% HCl heat for diffusing over 1.0 hour. Upon cooling, after filtrating the extracted solids, 200% NaOH is added to alkalize.

The mixed solution's organic layer is extracted with chloroform and filtrating the extracted solids with potassium carbonate solution. The generated product is filled into silica gel columns utilizing the ratio of ethyl acetate as the diluent; upon purification, guaiacoxyethylamine is obtained.

EXAMPLE 5

Synthesis Compound of Vanillindilol

Dissolved 6.6 grams (0.03 mol) vanillin epoxide, 5.0 grams (0.3 mol) guaiacoxyethylamine HCl in 300 ml absolute alcohol, and stirred 2 hours at room temperature. The generated product is filled into silica gel columns utilizing the ratio of ethyl acetate:n-hexane=1:1 as the diluent; upon purification, n-hexane is used for re-crystallization until white crystallization Vanillindilol are obtained.

EXAMPLE 6

Synthesis Compound of Vanidipine

Dissolved 0.01 mole Vanillindilol and 0.02 mole methyl acetoacetate in the mixture solution of 15 ml ethanol and 100 ml concentration ammonia. Then added for diffusion at 55° C. for 15 hours.

The mixed solution's organic layer is extracted with chloroform and filtrating the extracted solids with potassium carbonate solution. The generated product is filled into silica gel columns utilizing the ratio of ethyl acetate as the diluent; upon purification, vanidipine are obtained.

EXAMPLE 7

Synthesis Compound of Vanidipine Epoxide 15 grams of vanidipine and 900 ml of ethanol are placed in a bottle, and an equal molar of potassium hydroxide in 100 ml MeOH is added for reaction at 70° C. for 1 hour; 5 times molar of epichlorohydrine is added for diffusion at same condition for two hours. Upon reaction and pressurized reduction, it is heated until it dissolves and upon filtration. The generated product is filled into silica gel columns utilizing the ratio of ethyl acetate:n-hexane=1:1 as the diluent; upon purification, vinillin epoxide are obtained.

EXAMPLE 8

Synthesis Compound of Labedipinedilol-A (4-hydroxy-3-methoxybenzyl)-3,5-dicarboethoxy-1, 4-dihydropyridine]

Dissolved 0.01 mole Vanillindilol and 0.02 mole methyl acetoacetate in the mixture solution of 15 ml ethanol and 10 ml concentration ammonia. Then added for diffusion at 55° C. for 15 hours.

The mixed solution's organic layer is extracted with chloroform and filtrating the extracted solids with potassium carbonate solution. The generated product is filled into silica gel columns utilizing the ratio of ethyl acetate as the diluent; upon purification, Labedipinedilol-A is obtained.

EXAMPLE 9

Synthesis Compound of KMUP880723

Dissolved 0.01 mole p-hydroxybenzaldehyde and 1.2 times molar of NaOH in ethanol. Then added for diffusion at 60° C. for 1.5 hours; 5 times molar of epichlorohydrine is added for diffusion 60° C. for 4 hours. TLC was used to ensure complete reaction. The solution obtained from the reaction was directly decompressed to concentrate and dehydrated to remove ethanol. The concentrated liquid was separated by silica gel filled column. Hexane:Ethylacetate= 7:3 was used as the eluent solution. Collected and directly decompressed to concentrate the eluent solution, to obtain the over-saturated. Then the mixture solution of ethyl acetate and hexane was used to re-crystallized, repeatedly to obtain purified 4-epoxybenzylaldehyde.

On the other hands, dissolved 6.6 grams (0.03 mol) 4-epoxybenzylaldehyd, 5.0 grams (0.03 mol) guaiacoxyethylamine in 30 ml of absolute alcohol. Then diffusion at room temperature for two hours. The solution obtained from the reaction was directly decompressed to concentrate and dehydrated to remove ethanol. the concentrated liquid was separated by silica gel filled column. The mixture solution of Hexane and Ethylacetate was used as the eluent solution. Collected and directly decompressed to concentrate the eluent solution, to obtain the white crystallized product. Then hexane was used to re-crystallized, repeatedly to obtain purified KMUP880723, that {N-4-oxy-[2-hydroxy-3-(2-methoxy-1-oxyethylaminobenzene)propoxy]} benzaldehyde is obtained.

EXAMPLE 10

Synthesis Compound of Labedipinediol-B

Dissolved 0.01 mole KMUP880723 and 0.02 mole methyl acetoacetate in the mixture solution of 15 ml ethanol and 10 ml concentration ammonia. Then added for diffusion at 55° C. for 15 hours.

The mixed solution's organic layer is extracted with chloroform and filtrating the extracted solids with potassium carbonate solution. The generated product is filled into silica gel columns utilizing the ratio of ethyl acetate as the diluent; upon purification, Labedipinediol-B is obtained.

EXAMPLE 11

Synthesis Compound of Vanipiperadilol

Dissolved 6.6 grams (0.03 mol) vanillin epoxide, 5.0 grams (0.03 mol) 1-(2-chlorophenyl) piperazine in 30 ml of absolute alcohol. Then diffusion at room temperature for two hours. The solution obtained from the reaction was directly decompressed to concentrate and dehydrated to remove ethanol. the concentrated liquid was separated by silica gel filled column. Then ethyl acetate was used to re-crystallized, repeatedly to obtain purified Vanipiperadilol.

EXAMPLE 12

Synthesis Compound of Labedipinedilol-C

Dissolved 0.01 mol Vanipiperadilol and 0.02 mol methyl acetoacetate in the mixture solution of 15 ml ethanol and 10 ml concentration ammonia.Then diffusion at 55° C. for 15 hours. The solution obtained from the reaction was directly decompressed to concentrate and dehydrated to remove ethanol. the concentrated liquid was separated by silica gel filled column. Then ethyl acetate was used to re-crystallized, repeatedly to obtain purified Labedipinedilol-C.

EXAMPLE 13

Synthesis Compound of 2-(2-methylphenoxy) ethyl amine)

(1) 2-(2-methylphenoxy)ethylbromide 22.4 ml (0.2 mole) of 2-methyiphenol and 34.6 ml (0.4 mole) of ethylene dibromide are mixed and heated at 100° C. The mixture is stirred vigourously with 125 ml 1.6N NaOH, continued heat and stirred till the pH value to 7. Upon cooling, after filtrating the extracted solids, the mixed solution's organic layer is extracted with chloroform and rinsing the extracted solids with NaCl and MgSO4. The generated product is filled into silica gel chromatography columns. The mixture solution of Hexane and Ethylacetate was used as the eluent solution. Upon purification, until white crystallization 2-methyphenoxy)ethylbromide are obtained.

(2) (N-[2-(2-methylphenoxy)ethyl]phthalimide)

36 grams (0.156 ml) of 2-(2-methylphenoxy) ethylbromide and 27.3 grams (0.186 mole) of phthalimide are dissolved in 100 ml of dimethylacetamide, and stirred with heat for diffusion to 90° C. After 30 minutes, 10.45 g (0.186 mole) of potassium hydroxide (KOH) is dissolved in 30 ml of methanol solution for heating and diffusing over 1.5 hours. Upon cooling, the mixed solution is poured into 300 ml of water. After filtrating the extracted solids, 200 ml of 10% potassium carbonate ($K_2CO_3$) solution is added, and stirred with heat. The paste-like substance obtained is filtrated. After rinsing with tap water several times, moisture-free alcohol is used for re-crystallization until white crystallization is obtained.

(3)2-(2-methylphenoxy)ethylamine 21.0 grams (0.071 ml) of N-[2-(2-methylphenoxy)ethyl] phthalimide and 3.55 grams (0.071 mol) of hydrazine hydrate are dissolved in 70 ml of moisture-free alcohol for heating and diffusing over 45 minute. And stirred with 20 ml 18% HCl heat for diffusing over 1.0 hour. Upon cooling, after filtrating the extracted solids, 20% NaOH is added to alkalize. The mixed solution's organic layer is extracted with chloroform and filtrating the extracted solids with potassium carbonate solution. The generated product is filled into silicone tubes by utilizing the ratio of ethyl acetate as the diluent; upon purification, 2-(2-methylphenoxy) ethylamine are obtained.

EXAMPLE 14

Synthesis Compound of Vanillidilol

Dissolved 6.6 grams (0.03 mol) vanillin epoxide, 5.0 grams (0.03 mol) 2-(2-methylphenoxy)ethylamine in 30 ml absolute alcohol, and stirred 2 hours at room temperature.

The generated product is filled into silica gel columns utilizing the ratio of ethyl acetate and n-hexane as the diluent; upon purification, n-hexane is used for re-crystallization until white crystallization Vanillidilol is obtained.

EXAMPLE 15

Synthesis Compound of Labedipinediol-D

Dissolved 0.01 mole Vanillindilol and 0.02 mole methyl acetoacetate in the mixture solution of 15 ml ethanol and 10 ml concentration ammonia. Then added for diffusion at 55° C. for 15 hours.

The mixed solutions organic layer is extracted with chloroform and filtrating the extracted solids with potassium carbonate solution. The generated product is filled into silica gel columns utilizing the ratio of ethyl acetate as the diluent; upon purification, Labedipinediol-D is obtained.

EXAMPLE 16

Synthesis Compound of 2-chlorophenoxy Ethylamine
(1) 2(2-chlorophenoxy)ethylbromide 22.4 ml (0.2 mole) of 2-chlorophenol and 34.6 ml (0.4 mole) of ethylene dibromide are mixed and heated at 100° C. The mixture is stirred vigourously with 125 ml 1.6N NaOH, continued heat and stirred till the pH value to 7. Upon cooling, after filtrating the extracted solids, the mixed solution's organic layer is extracted with chloroform and rinsing the extracted solids with NaCl and MgSO4. The generated product is filled into silica gel chromatography columns. The mixture solution of Hexane and Ethylacetate was used as the eluent solution. Upon purification, until white crystallization 2(2-chlorophenoxy)ethylbromide is obtained.
(2) (N-[2-(2-chlorophenoxy)ethyl]phthalimide)

36 grams (0.156 ml) of 2-(2-chlorophenoxy)ethylbromide and 27.3 grams (0.186 mole) of phthalimide are dissolved in 100 ml of dimethylacetamide, and stirred with heat for diffusion to 90° C. After 30 minutes, 10.45 g (0.186 mole) of potassium hydroxide (KOH) is dissolved in 30 ml of methanol solution for heating and diffusing over 1.5 hours. Upon cooling, the mixed solution is poured into 300 ml of water. After filtrating the extracted solids, 200 ml of 10% potassium carbonate ($K_2CO_3$) solution is added, and stirred with heat. The paste-like substance obtained is filtrated. After rinsing with tap water several times, moistlure-free alcohol is used for re-crystallization until white crystallization is obtained.
(3) 2-chlorophenoxy Ethylamine 21.0 grams (0.071 ml) of N-[2-(2-chlorophenoxy)ethyl] phthalimide and 3.55 grams (0.071 mol) of hydrazine hydrate are dissolved in 70 ml of moisture-free alcohol for heating and diffusing over 45 minutes. And stirred with 20 ml 18% HCl heat for diffusing over 1.0 hour. Upon cooling, after filtrating the extracted solids, 20% NaOH is added to alkalize. The mixed solution's organic layer is extracted with chloroform and filtrating the extracted solids with potassium carbonate solution. The generated product is filled into silica gel columns utilizing the ratio of ethyl acetate as the diluent; upon purification, 2-(2-chlorophenoxy) ethylamine is obtained.

EXAMPLE 17

Synthesis Compound of Vanichlodilol

Dissolved 6.6 grams (0.3 mol) vanillin epoxide, 5.0 grams (0.3 mol) 2-chlorophenoxy ethylamine HCl in 30 ml absolute alcohol, and stirred 2 hours at room temperature. The generated product is filled into silica gel columns utilizing the ratio of ethyl acetate:n-hexane=1:1 as the diluent; upon purification, n-hexane is used for re-crystallization until white crystallization Vanillindilol is obtained.

EXAMPLE 18

Synthesis Compound of Labedipinediol-E

Dissolved 0.01 mole Vanichlodilol and 0.02 mole methyl acetoacetate in the mixture solution of 15 ml ethanol and 10 ml concentration ammonia. Then added for diffusion at 55° C. for 15 hours.

The mixed solution's organic layer is extracted with chloroform and filtrating the extracted solids with potassium carbonate solution. The generated product is filled into silica gel columns utilizing the ratio of ethyl acetate as the diluent; upon purification, vanidipine is obtained.

EXAMPLE 19

Another Synthesis Method Labedipinediol-A

Dissolved 0.01 mole vanidipine epoxide and 0.04 mole guaiacoxyethylamine in the mixture solution of 15 ml ethanol. Then added for diffusion at 55° C. for 1.0 hours. Upon reaction and pressurized reduction, it is heated until it dissolves and upon filtration. The generated product is filled into silica gel columns utilizing the ratio of ethyl acetate:n-hexane=1:1 as the diluent; upon purification, Labedipinediol-A is obtained.

EXAMPLE 20

Another Aynthesis Compound of Labedipinediol-B

Dissolved 0.01 mole 4-Hydroxybenzylaldehyde and 0.02 mole methyl acetoacetate in the mixture solution of 15 ml ethanol and 10 ml concentration ammonia. Then added for diffusion at 55° C. for 15 hours.

The mixed solution's organic layer is extracted with chloroform and filtrating the extracted solids with potassium carbonate solution. The generated product is filled into silica gel columns utilizing the ratio of ethyl acetate as the diluent; upon purification, 4-epoxybenzylaldehyde is obtained. Then mixed 0.02 mole 4-epoxybenzylaldehyde and 0.04 mole guaiacoxyethylamine in 15 ml ethanol, for diffusion at 55° C. for 15 hours.

The mixed solution's organic layer is extracted with chloroform and filtrating the extracted solids with potassium carbonate solution. The generated product is filled into silica gel columns utilizing the ratio of ethyl acetate as the diluent; upon purification, Labedipinediol-B is obtained.

EXAMPLE 21

Another Synthesis Compound of Labedipinediol-C

Dissolved 0.01 mole vanidipine epoxide and 0.04 mole 1-(2-chlorophenyl) piperazine in the mixture solution of 15 ml ethanol. Then added for diffusion at 55° C. for 1.0 hours. Upon reaction and pressurized reduction, it is heated until it dissolves and upon filtration. The generated product is filled into silica gel columns utilizing the ratio of ethyl acetate:n-hexane=1:1 as the diluent; upon purification, Labedipinediol-C is obtained.

EXAMPLE 22

Another Synthesis Compound of Labedipinediol-D

Dissolved 0.01 mole vanidipine epoxide and 0.04 mole 2-(2-methylphenoxy)ethylamine in the mixture solution of 15 ml ethanol. Then added for diffusion at 55° C. for 1.0 hours. Upon reaction and pressurized reduction, it is heated until it dissolves and upon filtration. The generated product is filled into silica gel columns utilizing the ratio of ethyl acetate:n-hexane=1:1 as the diluent; upon purification, Labedipinediol-D is obtained.

EXAMPLE 23

Another Synthesis Compound of Labedipinediol-E

Dissolved 0.01 mole vanidipine epoxide and 0.04 mole 2-Chlorophenoxyethylamine in the mixture solution of 15 ml ethanol. Then added for diffusion at 55° C. for 1.0 hours. Upon reaction and pressurized reduction, it is heated until it dissolves and upon filtration. The generated product is filled into silica gel columns utilizing the ratio of ethyl acetate:n-hexane=1:1 as the diluent; upon purification, Labedipinediol-E is obtained.

EXAMPLE 24

Synthesis Compound of 2(2-trifluoromethylphenoxy) ethylamine 22.4 ml (0.2 mole) of 2-trifluoromethylphenol and 34.6 ml (0.4 mole) of 2-Bromoethylamine mixing, and heating at 100° C. And violent stirred with 125 ml 1.6N NaOH, continued heat and stirred till the pH value to 7. Upon cooling, after filtrating the extracted solids, the mixed solution's organic layer is extracted with chloroform and resing rinsing the extracted solids with NaCl and $MgSO_4$. The generated product is filled into silica gel chromatography columns. The mixture solution of Hexane and Ethylacetate was used as the eluent solution. Upon purification, until white crystallization 2(2-trifluoromethylphenoxy) ethylamine is obtained.

EXAMPLE 25

Synthesis Compound of Labedipinediol-F

Dissolved 0.01 mole vanidipine epoxide and 0.04 mole 2(2-trifluoromethylphenoxy)ethylamine in the mixture solution of 15 ml ethanol. Then added for diffusion at 55° C. for 1.0 hours. Upon reaction and pressurized reduction, it is heated until it dissolves and upon filtration. The generated product is filled into silica gel columns utilizing the ratio of ethyl acetate:n-hexane=1:1 as the diluent; upon purification, Labedipinediol-F is obtained.

EXAMPLE 26

Synthesis Compound of Labedipinediol-G

Dissolved 6.6 grams (0.3 mol) vanillin epoxide, 5.0 grams (0.03 mol) 2-(2-trifluroethoxyphenoxy)ethylamine HCl in 30 ml absolute alcohol, and stirred 2 hours at room temperature. The generated product is filled into silica gel columns utilizing the ratio of ethyl acetate:n-hexane=1:1 as the diluent; upon purification, n-hexane is used for re-crystallization until white crystallization flurovanidilol is obtained.

The tables which follow report data that relates to the present invention. Table 1 provides physicochemical data of the synthetic compounds. Table 2 reports blood pressure reduction results. Table 3 gives $pA_2$ and $pKCa^{-1}$ values and slopes of Schild Plots for test compounds in in vitro studies. Table 4 shows inhibition of [$^3$H]-ligand Specific Binding Sites by test compounds. Following are relevant footnotes and explanations: [a]Negative logarithm of molar concentration required displacing half of the radiolabelled ligand from specific sites; the results illustrated are the mean±s.e.m. of three experiments, each conducted in triplicate; [b]K values were calculated from the equation $K_i=IC_{500}/(1+[^3H]ligand/K_d)$. $K_d$ and [$^3$H]ligand denote the apparent dissociation constant and the free concentration of the radiolabel, respectively; [c]NT: not tested; $K_i=IC_{500}/(1+[^3H]ligand/K_d)$.

TABLE 1

| | vanillindilol |
|---|---|
| MS(Scan FAB+) | 375 |
| UV | 251.0 |
| IR | 3550-OH(alcohol), 3333-NH(amine), |
| | 3010, 2839-$CH_2$(aliphatic), |
| | 1129, 1029(—C—O), 763(-benzene) |
| $^1$H-NMR(CDCl$_3$) | δ 2.50~2.89 (m, 4H, —C$\underline{H}_2$—N—C$\underline{H}_2$—), |
| | 3.71~3.79 (d, 6H, 2 × Ar—O—C$\underline{H}_3$), |
| | 3.86~4.02 (m, 4H, Ar—O—C$\underline{H}_2$—), |
| | 4.19~4.24 (t, 1H, Ar—O—C$\underline{H}$(OH)—), |
| | 6.84~7.37 (m, 7H, Ar—$\underline{H}$), |
| | 8.309(s, 1H, C$\underline{H}$O) |
| | vanidipine |
| MS(Scan FAB+) | 309 |
| UV | 259.0 |
| IR | 3533-OH(alcohol), 3276-NH(amine), |
| | 2778-$CH_3$ (sp$^3$), 1651 (—C═O), |
| | 1127, 1023(—C—O), 810, 748 (-benzene) |
| $^1$H-NMR(CDCl$_3$) | δ 2.26(s, 6H, 2 × C$\underline{H}_3$), 3.56(s, 6H, 2CO—OC$\underline{H}_3$) |
| | 3.68–3.74(s, 3H, 1 × Ar—OC$\underline{H}_3$), |
| | 4.93(s, 1H, Ar—C$\underline{H}$<) 6.84–7.37(m, 3H, Ar—$\underline{H}$) |
| | vanidipine epoxide |
| MS(Scan FAB+) | 365 |
| UV | 259 |
| IR | 3276-NH(amine), 2778-$CH_3$ (sp$^3$), |
| | 1651 (—C═O), 1127, 1023 (—C—O), |
| | 810, 748 (-benzene) |
| $^1$H-NMR(CDCl$_3$) | δ 2.26(s, 6H, 2 × C$\underline{H}_3$), |
| | 2.77–2.97 (m, 2H, CH (O) C$\underline{H}_2$) |
| | 3.39–3.47 (m, 1H, C$\underline{H}$ (O) $CH_2$), |
| | 3.56(s, 6H, 2CO—OC$\underline{H}_3$) |

TABLE 1-continued

|  |  |
|---|---|
|  | 3.68–3.74(s, 3H, 1 × Ar—OC$\underline{H}_3$),<br>4.43(m, 2H, 1 × Ar—OC$\underline{H}_2$) 4.93(s, 1H, Ar—C$\underline{H}$<),<br>6.84–7.37(m, 3H, Ar—$\underline{H}$)<br>8.33(s, 1H, exchangeable, —N$\underline{H}$—) |
|  | Labedipinedilol-A |
| MS(Scan FAB+) | 570 |
| UV | 260 |
| IR | 3533-OH(alcohol), 3276-NH(amine),<br>2778-CH$_3$(sp$^3$), 1651(—C═O),<br>1127, 1023 (—C—O), 810, 748(-benzene) |
| $^1$H-NMR(CDCl$_3$) | δ 2.26(s, 6H, 2Xc$\underline{h}_3$),<br>2.50–2.89(m, 4H, C$\underline{H}_2$—NH—C$\underline{H}_2$),<br>3.56(s, 6H, 2CO—OC$\underline{H}_3$),<br>3.68–3.74(s, 6H, 2 × Ar—OC$\underline{H}_3$),<br>3.86–4.05(m, 4H, 2 × Ar—OC$\underline{H}_2$),<br>4.4(s, 1H, CH—O$\underline{H}$), 4.93(s, 1H, Ar—C$\underline{H}$<),<br>8.33(s, 1H, exchangeable, —N$\underline{H}$—),<br>6.84–7.37(m, 7H, Ar—$\underline{H}$), |
|  | MUP880723 |
| MS(Scan FAB+) | 345 |
| UV | 251.0 |
| IR | 3550-OH(alcohol), 3333-NH (amine),<br>3010, 2839-CH$_2$(aliphatic), 1129, 1029(—C—O),<br>763(-benzene) |
| $^1$H-NMR(CDCl$_3$) | δ 2.86–3.22(m, 4H, C$\underline{H}_2$—NH—C$\underline{H}_2$),<br>3.98–4.25(m, 4H, Ar—OC$\underline{H}_2$),<br>3.81–3.87(s, 3H, Ar—OC$\underline{H}_3$),<br>4.35(s, 1H, CH—O$\underline{H}$),<br>4.10–4.15(m, 4H, Ar—OC$\underline{H}_2$),<br>4.97(s, 1H, Ar—C$\underline{H}$<), 6.83–6.99(m, 7H, Ar—$\underline{H}$),<br>8.33(broad, 1H, exchangeable, C—N$\underline{H}$—C) |
|  | Labedipinediol-B |
| MS(Scan FAB+) | 540 |
| UV | 219.0 |
| IR | 3533-OH(alcohol), 3278-NH(amine),<br>2774-CH$_3$(sp$^3$), 1653(—C═O),<br>1125, 1024(—C—O), 809, 746(-benzene) |
| $^1$H-NMR(CDCl$_3$) | δ 2.35(s, 6H, 2 × C$\underline{H}_3$),<br>2.76–3.13(m, 4H, C$\underline{H}_2$—NH—C$\underline{H}_2$),<br>3.68(s, 6H, 2CO—OC$\underline{H}_3$),<br>3.78(s, 3H, Ar—OC$\underline{H}_3$), 3.89(s, 1H, CH—O$\underline{H}$),<br>4.13–4.19(m, 4H, Ar—OC$\underline{H}_2$)<br>4.93(s, 1H, Ar—C$\underline{H}$<),<br>5.97(s, 1H, exchangeable, —N$\underline{H}$—)<br>6.73–7.19(m, 7H, Ar—$\underline{H}$) |
|  | Vanipiperadilol |
| MS(Scan FAB+) | 404.5 |
| UV | 251.0 |
| IR | 3550-OH(alcohol), 3333-NH(amine),<br>3010, 2839-CH$_2$(aliphatic),<br>1129, 1029(—C—O), 763(-benzene) |
| $^1$H-NMR(CDCl$_3$) | δ 1.4~2.3 (broad, 1H, O$\underline{H}$),<br>2.728~2.762 (t, 4H, 2 × N—C$\underline{H}_2$),<br>2.916~3.016 (m, 2H, Ar— O—CH(OH)— C$\underline{H}_2$—N),<br>3.136~3.159 (t, 4H, 2 × N—C$\underline{H}_2$),<br>3.929 (s, 3H, Ar—O—C$\underline{H}_3$),<br>3.858~4.027 (d, 2H, Ar—O—C$\underline{H}_2$—),<br>4.164~4.336 (m, 1H, Ar— O—CH$_2$—C$\underline{H}$(OH)—),<br>6.953~7.476 (m, 7H, Ar—$\underline{H}$),<br>9.864 (s, 1H, C$\underline{H}$O), |
|  | Labedipinedilol-C |
| MS(Scan FAB+) | 599.5 |
| UV | 219.0 |
| IR | 3535-OH(alcohol), 3276-NH(amine),<br>2778-CH$_3$(sp$^3$), 1651 (—C═O),<br>1127, 1023 (—C—O) |
| $^1$H-NMR(CDCl$_3$) | δ 1.4~2.2 (broad, 1H, O$\underline{H}$), 2.342 (s, 6H, 2 × C$\underline{H}_3$)<br>2.703~2.814 (t, 4H, 2 × N—C$\underline{H}_2$)<br>2.896~2.973 (m, 2H, Ar— O—CH(OH)—C$\underline{H}_2$—N)<br>3.136–3.182 (t, 4H, 2 × N—C$\underline{H}_2$),<br>3.661 (s, 6H, 2 × COO—C$\underline{H}_3$) 3.820 (s, 3H, Ar—O—C$\underline{H}_3$),<br>3.985–4.024 (m, 2H, Ar—O—C$\underline{H}_2$—) |

TABLE 1-continued 4.196~4.235 (m, 1H, Ar—O—CH$_2$—C$\underline{H}$(OH)—),
4.959 (s, 1H, Ar—$\underline{H}$)
5.626 (s, 1H, —N$\underline{H}$—), 6.760~7.385 (m, 7H, Ar—$\underline{H}$)

Labedipinedilol-D

| | |
|---|---|
| MS(Scan FAB+) | 554 |
| UV | 219.0 |
| IR | 3535-OH(alcohol), 3276-NH(amine) |
| | 2778-CH$_3$(sp$^3$), 1651(—C═O), |
| | 1127, 1023(—C—O), 810, 748(-benzene) |
| $^1$H-NMR(CDCl$_3$) | δ 2.31(s, 6H, 2 × C$\underline{H}_3$), 2.81(s, 3H, 1 × CH$_3$, Ar—C$\underline{H}_3$) |
| | 2.78–3.08(m, 4H, C$\underline{H}_2$—NH—C$\underline{H}_2$), |
| | 3.63(s, 6H, 2CO—OC$\underline{H}_3$) |
| | 3.68–3.74(s, 3H, Ar—OC$\underline{H}_3$), 4.4(s, 1H, CH—O$\underline{H}$) |
| | 4.10–4.14(m, 4H, Ar—OC$\underline{H}_2$), 4.93(s, 1H, Ar—C$\underline{H}$<) |
| | 5.98(s, 1H, exchangeable, —N$\underline{H}$—), |
| | 6.73–7.17(m, 7H, Ar—$\underline{H}$) |

Labedipinedilol-E

| | |
|---|---|
| MS(Scan FAB+) | 574 |
| UV | 219.0 |
| IR | 3528-OH(alcohol), 3269-NH(amine), |
| | 2773-CH$_3$ (sp$^3$), 1648(—C═O), |
| | 1125, 1027(—C—O), 819, 747(-benzene) |
| $^1$H-NMR(CDCl$_3$) | δ 2.31 (s, 6H, 2 × C$\underline{H}_3$), |
| | 2.78–3.08 (m, 4H, C$\underline{H}_2$—NH—C$\underline{H}_2$) |
| | 3.63 (s, 6H, 2CO—OC$\underline{H}_3$), 3.68–3.74 (s, 3H, Ar—OC$\underline{H}_3$) |
| | 4.43 (s, 1H, CH—O$\underline{H}$), 4.10–4.14 (m, 4H, Ar—OC$\underline{H}_2$) |
| | 4.88 (s, 1H, Ar—C$\underline{H}$<), |
| | 5.89 (s, 1H, exchangeable, —N$\underline{H}$—) |
| | 6.69–7.23 (m, 7H, Ar—$\underline{H}$) |

Labedipinediol-G

| | |
|---|---|
| MS(Scan FAB+) | |
| UV | 223.0 |
| IR | 3528-OH(alcohol), 3269-NH (amine), |
| | 2773-CH$_3$ (sp$^3$), 1648(—C═O), |
| | 1125, 1027(—C—O), 819, 747(-benzene) |
| $^1$H-NMR(CDCl$_3$) | δ 2.33 (s, 6H, 2 × C$\underline{H}_3$), |
| | 2.78–3.10 (m, 4H, C$\underline{H}_2$—NH—C$\underline{H}_2$) |
| | 3.65 (s, 6H, 2CO—OC$\underline{H}_3$), 3.68–3.76 (s, 3H, Ar—OC$\underline{H}_3$) |
| | 4.45 (s, 1H, CH—O$\underline{H}$), 4.10–4.16 (m, 6H, Ar—OC$\underline{H}_2$) |
| | 4.90 (s, 1H, Ar—C$\underline{H}$<) |
| | 5.91 (s, 1H, exchangeable, —N$\underline{H}$—) |
| | 6.69–7.25 (m, 7H, Ar—$\underline{H}$) |

TABLE 2

| | Decrease of blood pressure |
|---|---|
| Compounds | Decrease of blood pressure (mmHg) |
| Labedipinedilol A | 80 ± 12 |
| Labedipinedilol B | 60 ± 15 |
| Labedipinedilol C | 50 ± 17 |
| Labedipinedilol D | 55 ± 9 |
| Labedipinedilol E | 58 ± 7 |

TABLE 3 pA$_2$ and pKCa$^{-1}$ Values and Slopes of Schild Plots for Test Compounds in In Vitro Studies

| | β$_1$ pA$_2$ value(Slope) | | β$_2$ | α$_1$ | Calcium |
|---|---|---|---|---|---|
| Labedipin- | Right | Left | pA$_2$ value(Slope) | | PKCa$^{-1}$ value |
| edilols | atrium[a] | atrium[a] | Trachea[a] | Aorta[a] | Aorta(Slope) |
| Labedipin-edilol-A | 7.18 ± 0.09 (0.98 ± 0.04) | 7.43 ± 0.15 (0.88 ± 0.06) | 6.83 ± 0.06 (0.73 ± 0.04) | 8.23 ± 0.05 (0.90 ± 0.07) | 8.46 ± 0.04 (0.87 ± 0.07)[c] |
| Labedipin- | 6.61 ± 0.11 | 6.81 ± 0.08 | 6.48 ± 0.07 | 7.55 ± 0.05 | 8.02 ± 0.04 |

TABLE 3-continued pA$_2$ and pKCa$^{-1}$ Values and Slopes of Schild Plots for Test Compounds in In Vitro Studies

| Labedipin-edilols | β$_1$ pA$_2$ value(Slope) | | β$_2$ pA$_2$ value(Slope) | α$_1$ | Calcium PKCa$^{-1}$ value |
|---|---|---|---|---|---|
| | Right atrium[a] | Left atrium[a] | Trachea[a] | Aorta[a] | Aorta(Slope) |
| edilol-B | (0.97 ± 0.10) | (0.83 ± 0.06) | (0.85 ± 0.03) | (1.01 ± 0.06) | (0.78 ± 0.07) |
| Labedipin-edilol-C | 7.01 ± 0.09 (1.02 ± 0.04) | 7.23 ± 0.07 (0.99 ± 0.03) | 5.54 ± 0.16 (0.92 ± 0.02) | 6.87 ± 0.08 (0.88 ± 0.04) | 8.12 ± 0.04 (0.64 ± 0.07) |
| Labedipin-edilol-D | 7.23 ± 0.03 (0.84 ± 0.03) | 6.31 ± 0.12 (1.12 ± 0.04) | 5.70 ± 0.06 (1.10 ± 0.06) | 7.23 ± 0.05 (0.90 ± 0.07) | 8.23 ± 0.06 (0.39 ± 0.05) |
| Labedipin-edilol-E | 6.24 ± 0.06 (1.12 ± 0.06) | 6.15 ± 0.09 (1.07 ± 0.05) | 5.07 ± 0.12 (0.65 ± 0.03) | 8.46 ± 0.05 (0.78 ± 0.07) | 8.08 ± 0.04 (0.47 ± 0.06) |
| Labedipin-edilol-G | 6.25 ± 0.04 (1.10 ± 0.05) | 6.15 ± 0.07 (1.04 ± 0.03) | 5.02 ± 0.11 (0.62 ± 0.01) | 8.33 ± 0.02 (0.73 ± 0.04) | 8.02 ± 0.01 (0.47 ± 0.03) |

[a]pA$_2$ values were obtained from the formula pA$_2$ = [log (DR − 1) − log molar concentration antagonist] and the slope values were calculated from individual Schild plot by regression analysis. Each value was the mean ± S.E. of six to eight experimental results.
[b]The ratio values were obtained from the antilogarithm of the difference between the mean pA$_2$ values and pKCa$^{-1}$ values from in vitro studies.
[c]NT: not test.

What is claimed is:

1. A compound of the formula

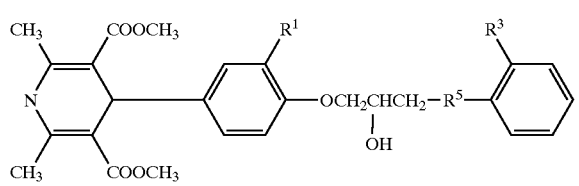

wherein $R^1$ is halogen or $C_{1-6}$-alkoxy, $R^3$ is hydrogen, halogen, $C_{1-6}$-alkyl, $C_{1-6}$-alkoxy, trifluoromethyl, or $CF_3(CH_2)_nO$— wherein n is 1, 2, of 3, and $R^5$ is

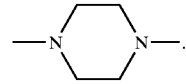

2. The compound of claim 1, wherein halogen is selected from the group consisting of fluorine, chlorine, bromine and iodine.

3. The compound of claim 1, wherein $R^1$ is methoxy and $R^3$ is chloro, namely, Labedipinedilol C.

4. A method of continuously maintaining hypotensive activity, which method comprises the step of treating a patient with a compound of claim 1, in a formulation containing diluents and/or excipients.

5. A compound of the formula

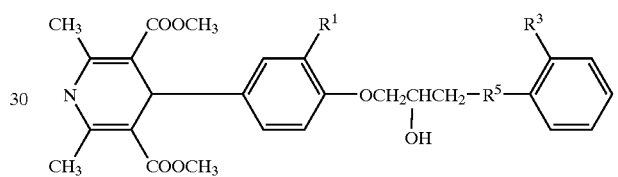

wherein $R^1$ is $C_{1-6}$-alkoxy, $R^3$ is hydrogen, halogen, $C_{1-6}$alkyl, trifluoromethyl, or $CF_3(CH_2)_nO$— wherein n is 1, 2, or 3, and $R^5$ is —NHCH$_2$CH$_2$O—.

6. The compound of claim 5, wherein halogen is selected from the group consisting of fluorine, chlorine, bromine and iodine.

7. The compound of claim 5, wherein $R^1$ is methoxy and $R^3$ is methyl, namely, Labedipinedilol D.

8. The compound of claim 5, wherein $R^1$ is methoxy and $R^3$ is chloro, namely, Labedipinedilol E.

9. The compound of claim 5, wherein $R^1$ is methoxy and $R^3$ is trifluoromethyl, namely, Labedipinedilol F.

10. The compound of claim 5, wherein $R^1$ is methoxy and $R^3$ is trifluoroethoxy, namely, Labedipinedilol G.

11. A method of continuously maintaining hypotensive activity, which method comprises the step of treating a patient with a compound of claim 5, in a formulation containing diluents and/or excipients.

* * * * *